United States Patent [19]

Goldmann et al.

[11] Patent Number: 4,786,641

[45] Date of Patent: Nov. 22, 1988

[54] DIHYDROPYRIDINE COMPOUNDS AND THEIR USE IN REDUCING BLOOD SUGAR

[75] Inventors: Siegfried Goldmann; Hans-Jürgen Ahr; Walter Puls; Hilmar Bischoff, all of Wuppertal; Dieter Petzinna, Duesseldorf; Klaus Schlossmann; Joachim Bender, both of Wuppertal, all of Fed. Rep. of Germany

[73] Assignee: Bayer Aktiengesellschaft, Leverkusen, Fed. Rep. of Germany

[21] Appl. No.: 87,491

[22] Filed: Aug. 20, 1987

[30] Foreign Application Priority Data

Aug. 30, 1986 [DE] Fed. Rep. of Germany ....... 3629545

[51] Int. Cl.$^4$ .................... A61K 31/44; C07D 211/90; C07D 491/048
[52] U.S. Cl. .................................. 514/302; 514/334; 514/336; 514/337; 514/356; 514/235.5; 544/124; 544/127; 546/116; 546/257; 546/258; 546/269; 546/284; 546/321
[58] Field of Search ................ 544/124, 127; 546/116, 546/257, 258, 269, 284, 321; 514/236, 302, 334, 336, 337, 356

[56] References Cited

U.S. PATENT DOCUMENTS 3,905,983  9/1975  Bossert et al. ..................... 546/321
3,970,662  7/1976  Carabateas et al. ............. 260/295.5

FOREIGN PATENT DOCUMENTS 3445356  6/1985  Fed. Rep. of Germany .
2201095  4/1974  France .
0125803 11/1984  United Kingdom .
0158138  3/1985  United Kingdom .
0161221  5/1985  United Kingdom .

Primary Examiner—Richard A. Schwartz
Assistant Examiner—Bernard I. Dentz

Attorney, Agent, or Firm—Sprung Horn Kramer & Woods

[57] ABSTRACT

Blood-sugar-lowering dihydropyridines of the formula

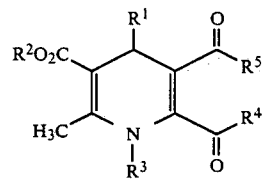

in which $R^1$ represents phenyl, naphthyl, thienyl, pyridyl, chromenyl or thiochromenyl, it being possible for the radicals mentioned each to carry up to 2 identical or different substituents from the series comprising halogen, alkyl, alkoxy and alkylthio with in each case up to 6 carbon atoms, fluoroalkyl and fluoroalkoxy with in each case up to 3 carbon atoms and 3 fluorine atoms, nitro and cyano, $R^2$ represents straight-chain, branched or cyclic alkyl which has up to 8 carbon atoms, can be interrupted in the alkyl chain by an oxygen or a sulphur atom and can be substituted by halogen, phenyl, cyano, hydroxyl, amino, alkylamino or dialkylamino with in each case up to 3 carbon atoms per alkyl group or by N-benzylmethylamino, $R^3$ represents straight-chain, branched or cyclic alkyl which has up to 6 carbon atoms, can be interrupted in the alkyl chain by an oxygen atom and can be substituted by halogen, hydroxyl, amino, phenyl, morpholino, carboxy or alkoxycarbonyl with up to 4 carbon atoms and $R^4$ and $R^5$ each represent hydroxyl, or $R^4$ and $R^5$ together represent —O—, or a physiologically acceptable salt thereof.

9 Claims, No Drawings

DIHYDROPYRIDINE COMPOUNDS AND THEIR USE IN REDUCING BLOOD SUGAR

The invention relates to dihydropyridine compounds, processes for their preparation and their use in medicaments, in particular medicaments which influence the blood sugar.

The present invention relates to dihydropyridine compounds of the general formula (I)

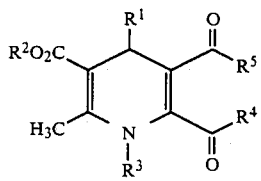

in which
R$^1$ represents phenyl, naphthyl, thienyl, pyridyl, chromenyl or thiochromenyl, it being possible for the radicals mentioned each to carry up to 2 identical or different substituents from the series comprising halogen, alkyl, alkoxy and alkylthio with in each case up to 6 carbon atoms, fluoroalkyl and fluoroalkoxy with in each case up to 3 carbon atoms and 3 fluorine atoms, nitro and cyano,
R$^2$ represents straight-chain, branched or cyclic alkyl which has up to 8 carbon atoms, can be interrupted in the alkyl chain by an oxygen or a sulphur atom and can be substituted by halogen, phenyl, cyano, hydroxyl, amino, alkylamino or dialkylamino with in each case up to 3 carbon atoms per alkyl group or by N-benzylmethylamino,
R$^3$ represents straight-chain, branched or cyclic alkyl which has up to 6 carbon atoms, can be interrupted in the alkyl chain by an oxygen atom and can be substituted by halogen, hydroxyl, amino, phenyl, morpholino, carboxy or alkoxycarbonyl with up to 4 carbon atoms and
R$^4$ and R$^5$ each represent hydroxyl, or
R$^4$ and R$^5$ together represent —O—,
in the form of their isomers, isomer mixtures, optical antipodes or racemates, and their physiologically acceptable salts.

Preferred compounds of the general formula (I) which may be mentioned are those in which
R$^1$ represents phenyl or thienyl, it being possible for the radicals mentioned to carry up to 2 identical or different substituents from the series comprising fluorine, chlorine, alkyl, alkoxy with in each case up to 3 carbon atoms, trifluoromethyl, nitro and cyano,
R$^2$ represents straight-chain or branched alkyl which has up to 6 carbon atoms, can be interrupted by an oxygen atom in the alkyl chain and can be substituted by fluorine, chlorine or phenyl,
R$^3$ represents straight-chain or branched alkyl which has up to 6 carbon atoms and can be substituted by hydroxyl or alkoxycarbonyl with up to 2 carbon atoms and
R$^4$ and R$^5$ each represent hydroxyl, or
R$^4$ and R$^5$ together represent —O—,
in the form of their isomers, isomer mixture, optical antipodes or racemates, and their physiologically acceptable salts.

Particularly preferred compounds of the general formula (I) which may be mentioned are those in which
R$^1$ represents phenyl, which can be substituted by up to 2 identical or different substituents from the group comprising chlorine, alkyl with up to 3 carbon atoms, trifluoromethyl or nitro,
R$^2$ represents straight-chain or branched alkyl which has up to 4 carbon atoms and can be interrupted in the alkyl chain by an oxygen atom,
R$^3$ represents straight-chain or branched alkyl with up to 4 carbon atoms and
R$^4$ and R$^5$ each represent hydroxyl, or
R$^4$ and R$^5$ together represent —O—,
in the form of their isomers, isomer mixtures, optical antipodes or racemates and their physiologically acceptable salts.

The compounds according to the invention exist in stereoisomeric forms which either behave as mirror images (enantiomers) or do not behave as mirror images (diastereomers). The invention relates both to the antipodes and to the racemic forms as well as the diastereomer mixtures. The racemic forms, like the diastereomers, can be resolved into the stereoisomerically uniform constituents in a known manner (compare E. L. Eliel, Stereochemistry of Carbon Compounds, McGraw Hill, 1962).

The dihydropyridinedicarboxylic anhydrides in the context of the general formula (I) correspond to the formula (Ia)

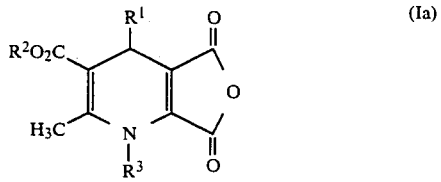

and the dihydropyridinedicarboxylic acids in the context of the general formula (I) correspond to the formula (Ib)

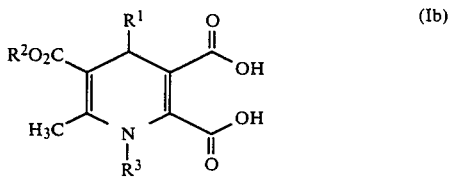

The compounds according to the invention can be in the form of their salts. Physiologically acceptable salts of the dihydropyridinedicarboxylic acid anhydrides are in general salts of the substances (Ia) according to the invention with inorganic or organic salts. Examples which may be mentioned are: hydrohalides, bisulphates, sulphates, hydrogen phosphates, acetates, maleates, citrates, fumarates, tartrates, lactates or benzoates.

Physiologically acceptable salts of the dihydropyridinedicarboxylic acids (Ib) can be metal salts or ammonium salts of the substances according to the invention. Particularly preferred salts are, for example, the sodium, potassium, magnesium or calcium salts, and ammonium salts which are derived from ammonia or organic amines, such as, for example, ethylamine, di- or tri-ethylamine, di- or triethanolamine, dicyclohexylamine, dimethylaminoethanol, arginine or ethylenediamine.

The dihydropyridinedicarboxylic acid anhydrides of the general formula (Ia) according to the invention can be prepared by a process in which dihydropyridine-lactols of the general formula (II)

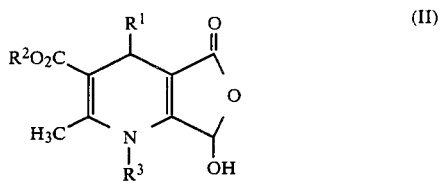

in which $R^1$, $R^2$ and $R^3$ have the meaning given, are oxidized in inert solvents.

If ethyl 4-(2-chlorophenyl)-1-ethyl-7-hydroxy-2-methyl-5-oxo-1,4,5,7-tetrahydrofuro[3,4-b]pyridine-3-carboxylate is used as the starting substance, the reaction can be illustrated by the following equation:

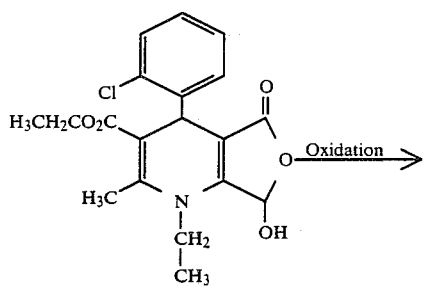

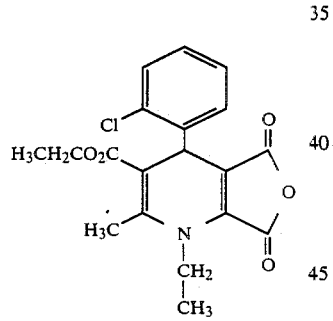

The oxidation is in general carried out with dimethylsulphoxide as the oxidizing agent in the presence of an activating agent in suitable solvents.

Activating agents which can be employed are carboxylic acid anhydrides, preferably acetic anhydride or trifluoroacetic anhydride, carboxylic acid halides, preferably oxalyl chloride, or dicyclohexylcarbodiimide/phosphoric acid, pyridinesulphurtrioxide-complex, phosphorus pentoxide or chlorosulphonyl isocyanate.

Suitable solvents are the customary solvents which do not change under the reaction conditions. These include, preferably, hydrocarbons, such as benzene, toluene, xylene or hexane, or ethers, such as diethyl ether, dioxane or tetrahydrofuran, or halogenohydrocarbons, such as methylene chloride, chloroform, carbon tetrachloride, 1,2-dichloroethane or 1,2-dichloroethylene, or mixtures of the solvents mentioned.

The oxidation is particularly preferably carried out with dimethylsulphoxide as the oxidizing agent in the presence of trifluoroacetic anhydride. It has proved advantageous here for dimethylsulphoxide to be simultaneously used as the solvent in a large excess.

The oxidation can moreover also be carried out with oxidizing agents such as chromium(VI) compounds, preferably with chromium(VI) oxide in dilute sulphuric acid/acetone, acetic acid or pyridine, and sodium dichromate or potassium dichromate, manganese dioxide or potassium permanganate, such as is described in Houben-Weyl's "Methoden der organischen Chemie" ("Methods of Organic Chemistry") Volume IV/1a, 1b.

The process according to the invention is in general carried out in a temperature range from $-30°$ C. to $+60°$ C., preferably from $-10°$ C. to $+30°$ C.

The process according to the invention is in general carried out under normal pressure, but it is also possible for the process to be carried out under reduced pressure or under increased pressure.

The process according to the invention can be carried out, for example, as follows:

The dihydropyridine-lactol is dissolved in an excess of dimethylsulphoxide, and trifluoroacetic anhydride is added, with cooling. When the reaction is added, the mixture is worked up in the customary manner by extraction, chromatography and/or crystallization.

The compounds of the general formula (Ib) according to the invention

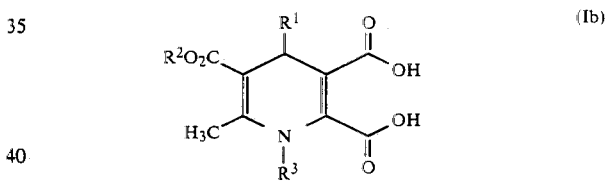

can be prepared by a process in which dihydropyridinedicarboxylic acid anhydrides of the general formula (Ia) in which $R^1$, $R^2$ and $R^3$ have the meaning given, are hydrolyzed and if appropriate the free acids are converted into their salts.

If ethyl 4-(2-chlorophenyl)-5,7-dioxo-1-ethyl-2-methyl-1,4,5,7-tetrahydrofuro[3,4-b]pyridine-3-carboxylate is used as the starting substance, the process can be illustrated by the following equation:

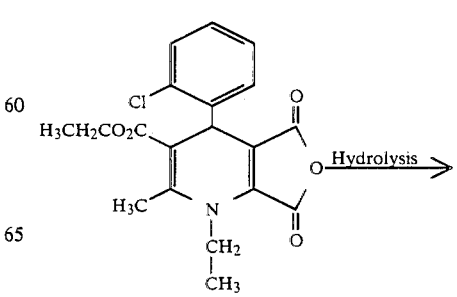

-continued

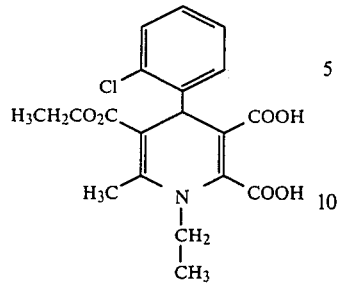

The hydrolysis is in general carried out with the aid of bases in suitable solvents.

Suitable bases are the customary basic compounds. These include, preferably, alkali metal or alkaline earth metal hydroxides, such as sodium hydroxide, potassium hydroxide or barium hydroxide, or alkali metal carbonates, such as sodium carbonate, sodium bicarbonate or potassium carbonate, or alkali metal alcoholates, such as sodium methanolate, potassium methanolate, sodium ethanolate, potassium ethanolate or potassium tert.-butylate, or ammonia or organie amines, such as triethylamine or diisopropylamine.

Suitable solvents are the customary solvents which do not change under the reaction conditions. These include, preferably, water of alcohols, such as methanol, ethanol, propanol, isopropanol or butanol, or ethers, such as diethyl ether, dioxane or tetrahydrofuran, or dimethylformamide, hexamethylphosphoric acid triamide, acetone or acetonitrile. It is also possible to use mixtures of the solvents mentioned.

The hydrolysis is particularly preferably carried out with aqueous alkali metal hydroxide solutions, such as, for example, potassium hydroxide solution or sodium hydroxide solution in alcohols, such as, for example, methanol, ethanol, propanol, isopropanol or butanol, as the solvent.

The hydrolysis is carried out in a temperature range from 0° C. to +100° C., preferably from +20° C. to +60° C.

The hydrolysis can be carried out under normal pressure, under increased pressure or under reduced pressure. It is in general carried out under normal pressure.

The base is in general employed in an amount of 2 to 6 mols, preferably 2 to 4 mols per mol of the dihydropyridinedicarboxylic acid anhydride.

It has proved advantageous here to use the base in an amount of at least 2 mols per mol of the dihydropyridinedicarboxylic acid anhydride and to prepare the corresponding salts in one step.

The process can be carried out, for example, as follows:

The dihydropyridinedicarboxylic acid anhydride is dissolved in a suitable solvent, and the corresponding base is added. Working up is effected in the customary manner.

The dihydropyridine-lactols of the general formula (II) employed as starting substances can be prepared by a process in which

[A] formyl compounds of the general formula (III)

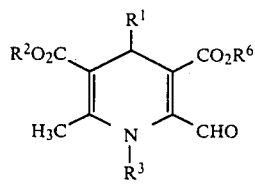

in which
R$^1$, R$^2$ and R$^3$ have the meaning given and
R$^6$ represents straight-chain or branched alkyl with up to 8 carbon atoms,
are reacted first with a base and then with an acid in suitable solvents, or by a process in which

[B] dihydropyridine-lactones of the general formula (IV)

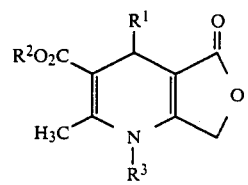

in which R$^1$, R$^2$ and R$^3$ have the meaning given, are brominated in suitable solvents, if appropriate in the presence of a base, and then hydrolyzed, or hydroxylated directly.

The preparation by process A or B of the starting substances (II) used according to the invention can be illustrated by the following equations, depending on the nature of the starting substances (III) and (IV) used:

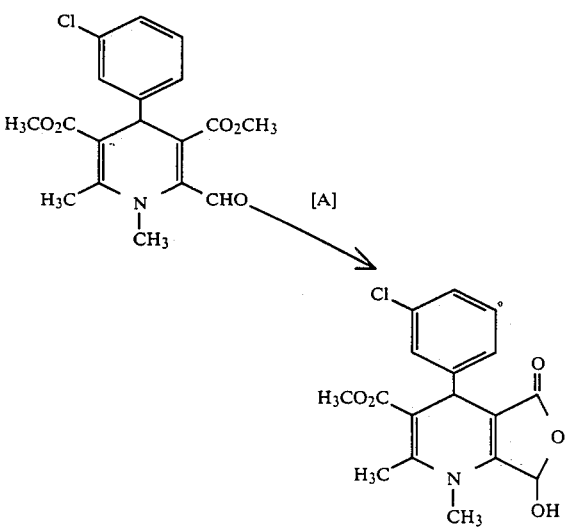

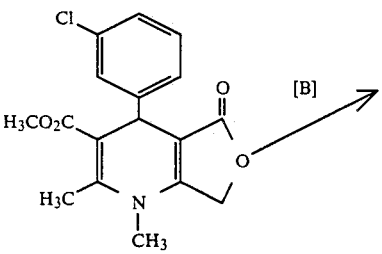

Process A:

Suitable solvents are water and all the organic solvents which do not change under the reaction conditions. These include, preferably, alcohols, such as methanol, ethanol, propanol, isopropanol or butanol, or ethers, such as diethyl ether, dioxane, tetrahydrofuran or glycol mono- or dimethyl ether, or acetonitrile, pyridine, dimethylformamide, dimethylsulphoxide or hexamethylphosphoric acid triamide. It is also possible to use mixtures of the solvents mentioned.

Suitable bases are the customary inorganic or organic bases. These include, preferably, alkali metal hydroxides, such as sodium hydroxide or potassium hydroxide, or alkali metal alcoholates, such as sodium methylate, sodium ethylate, potassium methylate, potassium ethylate or potassium tert.-butylate, or alkali metals, such as sodium, or alkali metal hydrides, such as sodium hydride or potassium hydride, or alkali metal amides, such as sodium amide or lithium diisopropylamide.

Possible acids are the customary organic or inorganic acids. These include, preferably, mineral acids, such as hydrochloric acid, hydrobromic acid, sulphuric acid or phosphoric acid, or organic carboxylic acids, such as acetic acid.

The procedure is carried out by first reacting the formyl compounds of the formula (III) with 100 to 5 mols, preferably with 50 to 10 mols, of base per mol of formyl compound in suitable solvents and then treating the reaction mixture with acids. The mixture is worked up in the customary manner.

The reaction is in general carried out at temperatures from 0° C. to +150° C., preferably from +20° C. to +100° C.

The reaction can be carried out under normal pressure or under increased or reduced pressure. It is in general carried out under normal pressure.

The formyl compounds of the general formula (III) employed as starting compounds are known or can be prepared by known methods [DOS (German Published Specification) No. 2,629,892].

Process B:

The bromination is carried out with the customary brominating agents, such as N-bromosuccinimide or bromine, preferably with bromine.

Suitable bases here are the customary basic compounds. These include, preferably, alkali metals, such as sodium or potassium, alkali metals hydrides, such as sodium hydride or potassium hydride, alkali metal amides, such as sodium amide or lithium diisopropylamide, or organometallic compounds, such as phenyllithium, n-butyllithium, sec.-butyllithium or tert.-butyllithium, or alcoholates, such as sodium ethanolate, sodium ethanolate, potassium methanolate, potassium ethanolate or potassium tert.-butanolate.

Suitable solvents are all the organic solvents which do not change under the reaction conditions. These include, preferably, ethers, such as diethyl ether, dioxane or tetrahydrofuran, or hydrocarbons, such as benzene, toluene, xylene, hexane or cyclohexane, or petroleum fractions. It is also possible to use mixtures of the solvents mentioned.

The bromination is carried out in a temperature range from −120° C. to +100° C., preferably from −80° C. to +50° C.

The bromination can be carried out, for example, by first producing an anion with 5 to 1 mol, preferably with 2 to 1 mol and particularly preferably with 1 mol, of base per mol of the starting compound (IV) and converting this anion into the bromide by means of bromine. Subsequent conversion of the bromine compound into the corresponding hydroxy compound of the general formula (II) is advantageously carried out without isolation of the bromine compound. The hydrolysis is carried out by water, if appropriate in the presence of traces of an acid, such as, for example, hydrochloric acid or sulphuric acid, in a manner which is known per se.

Process B can be carried out either under normal or under increased or reduced pressure. It is in general carried out under normal pressure.

However, the conversion of the compound (IV) into the compounds (II) can also be carried out by other methods which are known from the literature and is not limited to the processes described.

The hydroxylation can likewise be carried out by 2-sulphonyloxaziridine, with molybdenum peroxide/pyridine/phosphate or with oxygen/phosphite, in each case in the presence of bases in inert organic solvents, such as is described, for example, by E. Vedejs in J. Am. Chem. Soc. 96, 5944 (1974) or J. Org. Chem. 43, 188 (1978) or by J. M. Billmers, J. Finn in J. Org. Chem. 49, 3243 (1984) or by H. H. Wassermann, B. H. Lipschutz in Tetrahedron Letters 1975, 1731.

The lactones of the general formula (IV) used as starting compounds are known or can be prepared by known methods [DOS (German Published Specification) No. 3,410,645].

The compounds of the general formula (I) according to the invention exhibit a useful pharmacological action spectrum.

The hypoglycaemic action of the substances to be investigated was tested on male Wistar rats weighing between 140 and 190 g. For this purpose, the rats were fasted for 18 hours before administration of the substances. The substances to be investigated were dissolved in pure dimethylsulphoxide directly before administration. Pure dimethylsulphoxide (control animals) and the substances dissolved in dimethylsulphoxide were administered intravenously into the tail veins of the rats.

Blood was withdrawn from each rat from the retroorbital venus plexus 30, 60 and 120 minutes after the administration. 30 $\mu$l portions of blood were withdrawn with an automatic diluter and deproteinated with 0.3 ml of uranyl acetate (0.16%). After centrifugation, the glucose in the supernatant was determined photometrically on a Gemsaec Fast Analyzer by the glucose oxidase method using 4-amino-phenazone as the colour reagent. The results were evaluated by the Student t-test, and $p < 0.05$ was chosen as the significance limit.

Substances which effected a significant reduction in the blood glucose concentration of at least 10% at a point in time in the rats, compared with the control group which only received dimethylsulphoxide intravenously, were described as active.

The following Table 1 contains the changes found in the blood glucose concentrations as a percentage of the control.

TABLE 1

| Substance (Example No.) | Decrease in blood glucose concentration in % of the control 1 mg/kg of body weight i.v. |
|---|---|
| 2 | 22 |
| 3 | 23 |

The present invention includes pharmaceutical formulations which, in addition to non-toxic inert pharmaceutically suitable excipients, contain one or more compounds according to the invention or consist of one or more active compounds according to the invention and also includes processes for the preparation of these formulations.

The present invention also includes pharmaceutical formulations in dosage units. This means that the formulations are in the form of individual parts, for example tablets, dragees, capsules, pills, suppositories and ampules,. the active compound content of which corresponds to a fraction or a multiple of an individual dose. The dosage units can contain, for example, 1, 2, 3 or 4 individual doses or ½, ⅓, or ¼ of an individual dose. An individual dose preferably contains the amount of active compound which is given in one administration and which usually corresponds to a whole or one half, one third or one quarter of a daily dose.

By non-toxic inert pharmaceutically suitable excipients there are to be understood solid, semi-solid or liquid diluents, fillers for formulation auxiliaries of all types.

Tablets, dragees, capsules, pills, granules, suppositories, solutions, suspensions and emulsions, pastes, ointments, gels, creams, lotions, powders and sprays may be mentioned as preferred pharmaceutical formulations.

Tablets, dragees, capsules, pills and granules can contain the active compound or compounds alongside the customary excipients, such as (a) fillers and extenders, for example starch, lactose, sucrose, glucose, mannitol and silicic acid, (b) binders, for example carboxymethylcellulose, alginates, gelatine and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol or glycerol monostearate, (h) adsorbents, for example kaolin and bentonite, and (i) lubricants, for example talc, calcium stearate, magnesium stearate and solid polyethylene glycols, or mixtures of the substances listed under (a) to (i).

The active compound or compounds, if appropriate with one or more of the abovementioned excipients, can also be in microencapsulated form.

Suppositories can contain, alongside the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Solutions and emulsions can contain, alongside the active compound or compounds, the customary excipients, such as solvents, solubilizing agents and emulsifiers, for example water, ethyl alcohol, isopropyl alcohol, ethyl carbonate, ethyl acetate, benzyl alcohol, dimethylformamide, oils, in particular cottonseed oil, groundnut oil, maize germ oil, olive oil, castor oil and sesame oil, glycerol, glycerol formal, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain, alongside the active compound or compounds, the customary excipients, such as liquid diluents, for example water, ethyl alcohol or propylene glycol, or suspending agents, for example ethoxylated isostearyl alcohols, polyoxyethylene sorbitol and sorbitan esters, microcrystalline cellulose, aluminum metahydroxide, bentonite, agar-agar and tragacanth, or mixtures of these substances.

The formulation forms mentioned can also contain colouring agents, preservatives and smell- and taste-improved additives, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95 percent by weight of the total mixture.

The abovementioned pharmaceutical formulations can also contain other pharmaceutical active compounds in addition to the compounds according to the invention.

The abovementioned pharmaceutical formulations are prepared in the customary manner by known methods, for example by mixing the active compound or compounds with the excipient or excipients.

The present invention also includes the use of the compounds of the general formula (I) and/or salts thereof, and pharmaceutical formulations thereof which contain the compounds of the formula (I) and/or salts thereof in human and veterinary medicine for the prevention, alleviation and/or cure of the abovementioned diseases.

In general, it has proved advantageous both in human medicine and in veterinary medicine in administer the active compound or compounds according to the invention in total amounts of about 0.5 to 500, preferably 50 to 100 mg/kg of body weight every 24 hours, if appropriate in the form of several individual doses, in order to achieve the desired results. An individual dose preferably contains the active compound or compounds according to the invention in amounts of about 1 to about 80, in particular 3 to 30 mg/kg of body weight. However, it may be necessary to deviate from the dosages mentioned, and in particular to do so as a function of the nature and body weight of the subject to be treated, the nature and severity of the disease, the nature of the formulation and of the administration of the medicament and the period or interval within which administration takes place.

Thus in some cases it may be sufficient to manage with less than the abovementioned amount of active compound, whilst in other cases the abovementioned amount of active compound must be exceeded. The particular optimum dosage and mode of administration required for the active compounds can easily be specified by any expert on the basis of his expert knowledge.

PREPARATION EXAMPLES

I. Starting substance

Example 1

Isopropyl 4-(2-chlorophenyl)-1-ethyl-7-hydroxy-2-methyl-5-oxo-1,4,5,7-tetrahydrofuro[3,4-b]pyridine-3-carboxylate

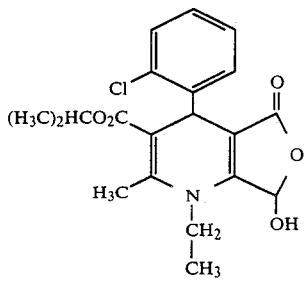

Process A:

5 mmol of 3-methyl 5-isopropyl 4-(2-chlorophenyl)-1-ethyl-2-formyl-6-methyl-1,4-dihydropyridine-3,5-dicarboxylate are taken in 40 mmol of 2N KOH and the mixture is warmed briefly at 40° C. in a waterbath. It is then subsequently stirred at room temperature for one hour. The solution is clarified with active charcoal and acidified with hydrochloric acid and the precipitate is filtered off with suction.

Yield: 30% of theory.
Melting point: 145°–147° C.

Process B:

60 mmol of diisopropylamine are taken in 100 ml of tetrahydrofuran. 50 mmol of butyllithium are added at a temperature of 0° C. under a stream of nitrogen. The mixture is then cooled to −78° C. and a solution of 50 ml of isopropyl 4-(2-chlorophenyl)-1-ethyl-2-methyl-5-oxo-1,4,5,7-tetrahydrofuro[3,4-b]pyridine-3-carboxylate (dissolved in tetrahydrofuran) is added dropwise. The mixture is stirred at −78° C. for 15 minutes, and this solution is pumped into a solution of 50 mmol of $Br_2$ and 50 ml of tetrahydrofuran with the aid of nitrogen, 50 mmol of cyclohexane are then immediately added, the mixture is allowed to warm to room temperature and is concentrated, the residue is dissolved in dimethylsulphoxide and water is added until the solution starts to become cloudy. The mixture is left to stand for 2 hours and the product is precipitated with water, filtered off with suction and separated with $CHCl_3$/MeOH 9:1 on silica gel.

Yield: 30% of theory.
Melting point: 145°–147° C.

II. End product

Example 2

Isopropyl 4-(2-chlorophenyl)-5,7-dioxo-1-ethyl-2-methyl-1,4,5,7-tetrahydrofuro[3,4-b]pyridine-3-carboxylate

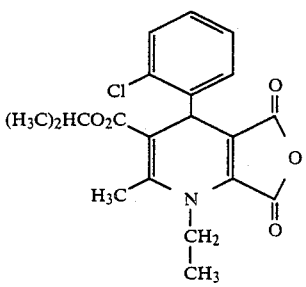

3.9 g (10 mmol) of isopropyl 4-(2-chlorophenyl)-1-ethyl-7-hydroxy-2-metthyl-5-oxo-1,4,5,7-tetrahydrofuro[3,4-b]pyridine-3-carboxylate are dissolved in 6 ml of absolute dimethylsulphoxide, 3 ml of trifluoroacetic anhydride are added, with cooling, and the mixture is stirred at room temperature for 1 hour. It is chromatographed rapidly on silica gel (toluene:ethyl acetate=88:2) and the yellow spot is isolated. After concentration, the residue is crystallized with a little methanol and the product is immediately filtered off with suction and dried.

Yield: 1.65 g (42.3% of theory).
Melting point: 87°–90° C.

Example 3

Disodium 3-isopropyl 4-(2-chlorophenyl)-1,4-dihydro-1-ethyl-2-methyl-pyridine-3,5,6-tricarboxylate

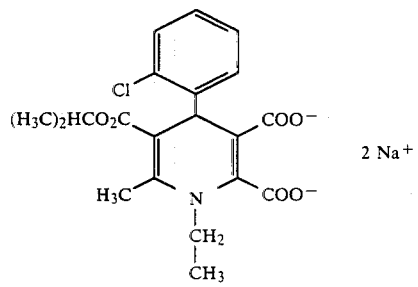

120 mg of isopropyl 4-(2-chlorophenyl)-5,7-dioxo-1-ethyl-2-methyl-1,4,5,7-tetrahydrofuro[3,4-b]pyridine-3-carboxylate are dissolved in 20 ml of tert.-butanol under the influence of heat and 2 equivalents of 0.2N aqueous sodium hydroxide solution are immediately added. The mixture is frozen and the product freeze-dried.

Yield: 120 mg.
Melting point: amorphous.

It will be understood that the specification and examples are illustrative but not limitative of the present invention and that other embodiments within the spirit and scope of the invention will suggest themselves to those skilled in the art.

We claim:

1. A dihydropyridine compound of the formula

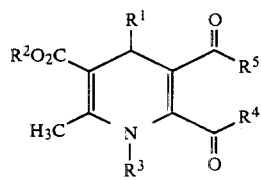

in which $R^1$ represents phenyl, naphthyl, thienyl, pyridyl, chromenyl or thiochromenyl, it being possible for the radicals mentioned each to carry up to 2 identical or different substituents from the series comprising halogen, alkyl, alkoxy and alkylthio with in each case up to 6 carbon atoms, fluoroalkyl and fluoroalkoxy with in each case up to 3 carbon atoms and 3 fluorine atoms, nitro and cyano, $R^2$ represents straight-chain, branched or cyclic alkyl which has up to 8 carbon atoms, can be interrupted in the alkyl chain by an oxygen or a sulphur atom and can be substituted by halogen, phenyl, cyano, hydroxyl, amino, alkylamino or dialkylamino with in each case up to 3 carbon atoms per alkyl group or by N-benzylmethylamino, R³ represents straight-chain, branched or cyclic alkyl which has up to 6 carbon atoms, can be interrupted in the alkyl chain by an oxygen atom and can be substituted by halogen, hydroxyl, amino, phenyl, morpholino, carboxy or alkoxycarbonyl with up to 4 carbon atoms and R⁴ and R⁵ each represent hydroxyl, or R⁴ and R⁵ together represent —O—, or a physiologically acceptable salt thereof.

2. A compound or salt according to claim 1, in which

R¹ represents phenyl or thienyl, it being possible for the radicals mentioned to carry up to 2 identical or different substituents from the series comprising fluorine, chlorine, alkyl, alkoxy with in each case up to 3 carbon atoms, trifluoromethyl, nitro and cyano, R² represents straight-chain or branched alkyl which has up to 6 carbon atoms, can be interrupted by an oxygen atom in the alkyl chain and can be substituted by fluorine, chlorine or phenyl, and R³ represents straight-chain or branched alkyl which has up to 6 carbon atoms and can be substituted by hydroxyl or alkoxycarbonyl with up to 2 carbon atoms.

3. A compound or salt according to claim 1, in which

R¹ represents phenyl, which can be substituted by up to 2 identical or different substituents from the group comprising chlorine, alkyl with up to 3 carbon atoms, trifluoromethyl and nitro, R² represents straight-chain or branched alkyl which has up to 4 carbon atoms and can be interrupted in the alkyl chain by an oxygen atom, and R³ represents straight-chain or branched alkyl with up to 4 carbon atoms.

4. A compound according to claim 1, wherein such compound is isopropyl 4-(2-chlorophenyl)-5,7-dioxo-1-ethyl-2-methyl-1,4,5,7-tetrahydrofuro[3,4-b]pyridine-3-carboxylate of the formula

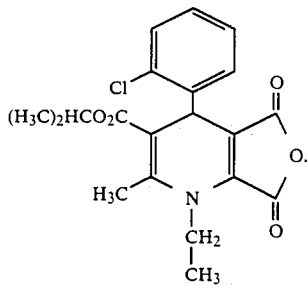

5. A compound according to claim 1, wherein such compound is disodium 3-isopropyl 4-(2-chlorophenyl)-1,4-dihydro-1-ethyl-2-methyl-pyridine-3,5,6-tricarboxylate of the formula

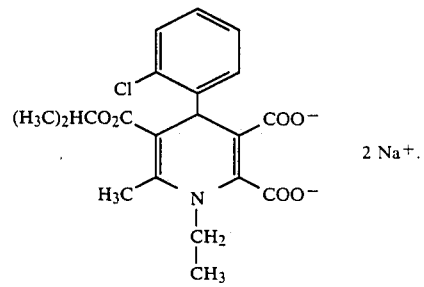

6. A blood-sugar lowering composition comprising a blood-sugar lowering effective amount of a compound or salt according to claim 1 and a diluent.

7. A unit dose of a composition according to claim 6 in the form of a tablet, capsule or ampule.

8. A method of reducing blood sugar in a patient in need thereof which comprises administering to such patient a blood-sugar lowering effective amount of a compound or salt according to claim 1.

9. The method according to claim 8, wherein such compound is
isopropyl 4-(2-chlorophenyl)-5,7-dioxo-1-ethyl-2-methyl-1,4,5,7-tetrahydrofuro[3,4-b]pyridine-3-carboxylate or
disodium 3-isopropyl 4-(2-chlorophenyl)-1,4-dihydro-1-ethyl-2-methyl-pyridine-3,5,6-tricarboxylate.

* * * * *

UNITED STATES PATENT AND TRADEMARK OFFICE
CERTIFICATE OF CORRECTION

PATENT NO. : 4,786,641

DATED : Nov. 22, 1988

INVENTOR(S) : Goldmann et al.

It is certified that error appears in the above-identified patent and that said Letters Patent is hereby corrected as shown below:

| | |
|---|---|
| Col. 4, line 27 | Delete "is added" and substitute --has ended-- |
| Col. 5, line 30 | Delete "of" and substitute --or-- |
| Col. 7, line 46 | Delete "metals" and substitute --metal-- |
| Col. 10, line 35 | Delete "in" in second instance and substitute --to-- |

Signed and Sealed this

Twenty-fourth Day of October, 1989

Attest:

DONALD J. QUIGG

Attesting Officer

Commissioner of Patents and Trademarks